US00PP34810P3

(12) United States Plant Patent
Olesen

(10) Patent No.: US PP34,810 P3
(45) Date of Patent: Dec. 13, 2022

(54) ROSE PLANT NAMED 'POULPAR126'

(50) Latin Name: *Rosa hybrida*
Varietal Denomination: Poulpar126

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredersburg (DK)

( * ) Notice: Subject to any disclaimer, the term of this patent is extended or adjusted under 35 U.S.C. 154(b) by 0 days.

(21) Appl. No.: 17/300,616

(22) Filed: Sep. 7, 2021

(65) Prior Publication Data

US 2022/0104418 P1 Mar. 31, 2022

(30) Foreign Application Priority Data

Sep. 21, 2020 (QZ) ..... PBR 2020/2269

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./102, 116, 122
See application file for complete search history.

*Primary Examiner* — Karen M Redden

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulpar126'.

This application claims priority to Plant Breeder's Rights Application Number 2020/2269, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpar126', originated as a single seedling from the stated cross.

The new variety may be distinguished from its male pollen parent and female seed parent primarily by the following characteristics. The male pollen parent plant has red flowers 80 mm in diameter while the new variety has red flowers 63 mm in diameter. The female seed parent plant has red flowers with 65 flower petals while the new variety has red flowers with 40 flower petals.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulpar126' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpar126' was selected in the spring of 2015 by the inventor as a single plant from the progeny of the aforementioned hybridization.

Asexual reproduction of 'Poulpar126' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpar126' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar126'.

Specifically illustrated in FIG. 1 of the drawings are open flowers, petals detached revealing reproductive flower parts and receptacle.

Figure 1:
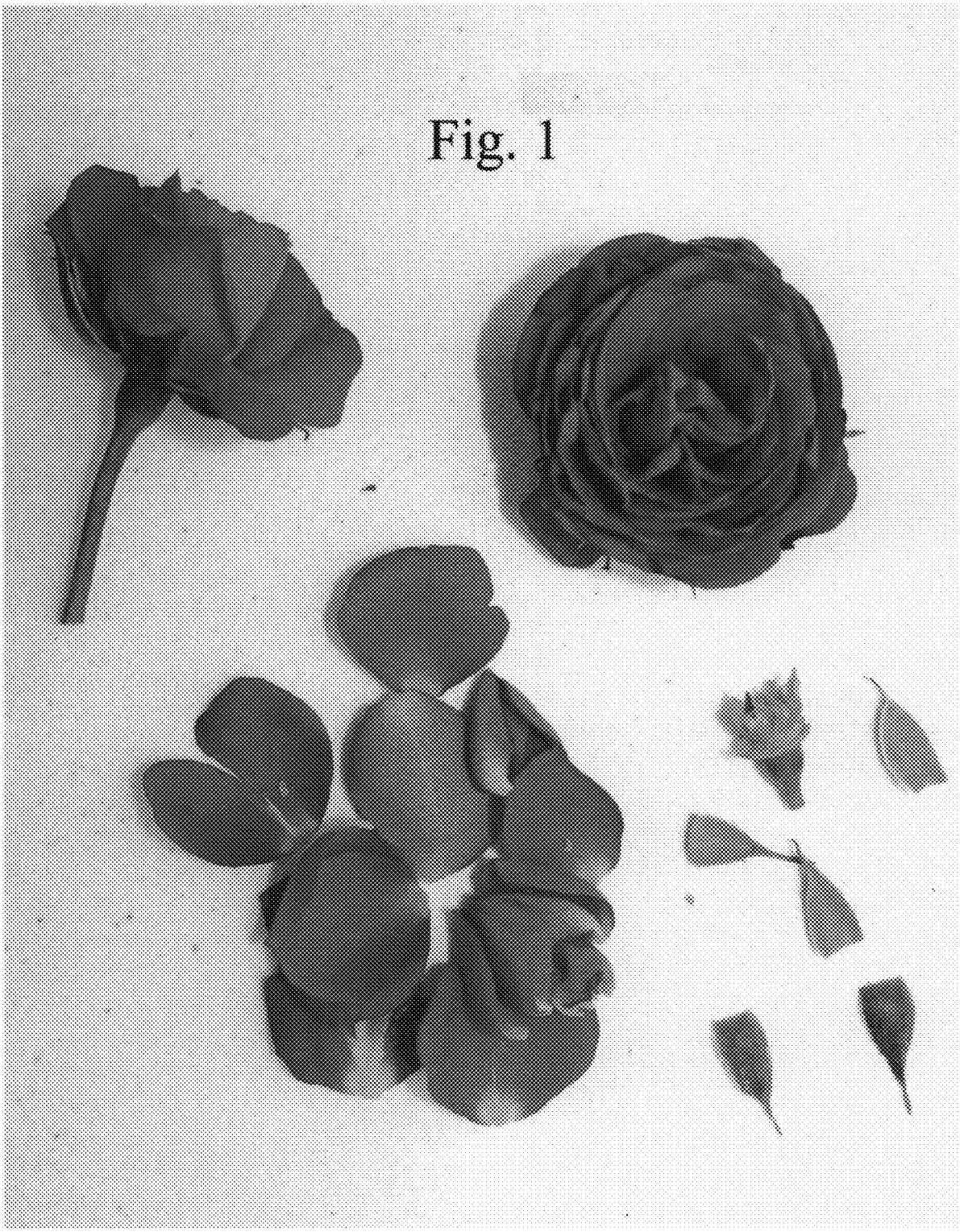
Figure 2:
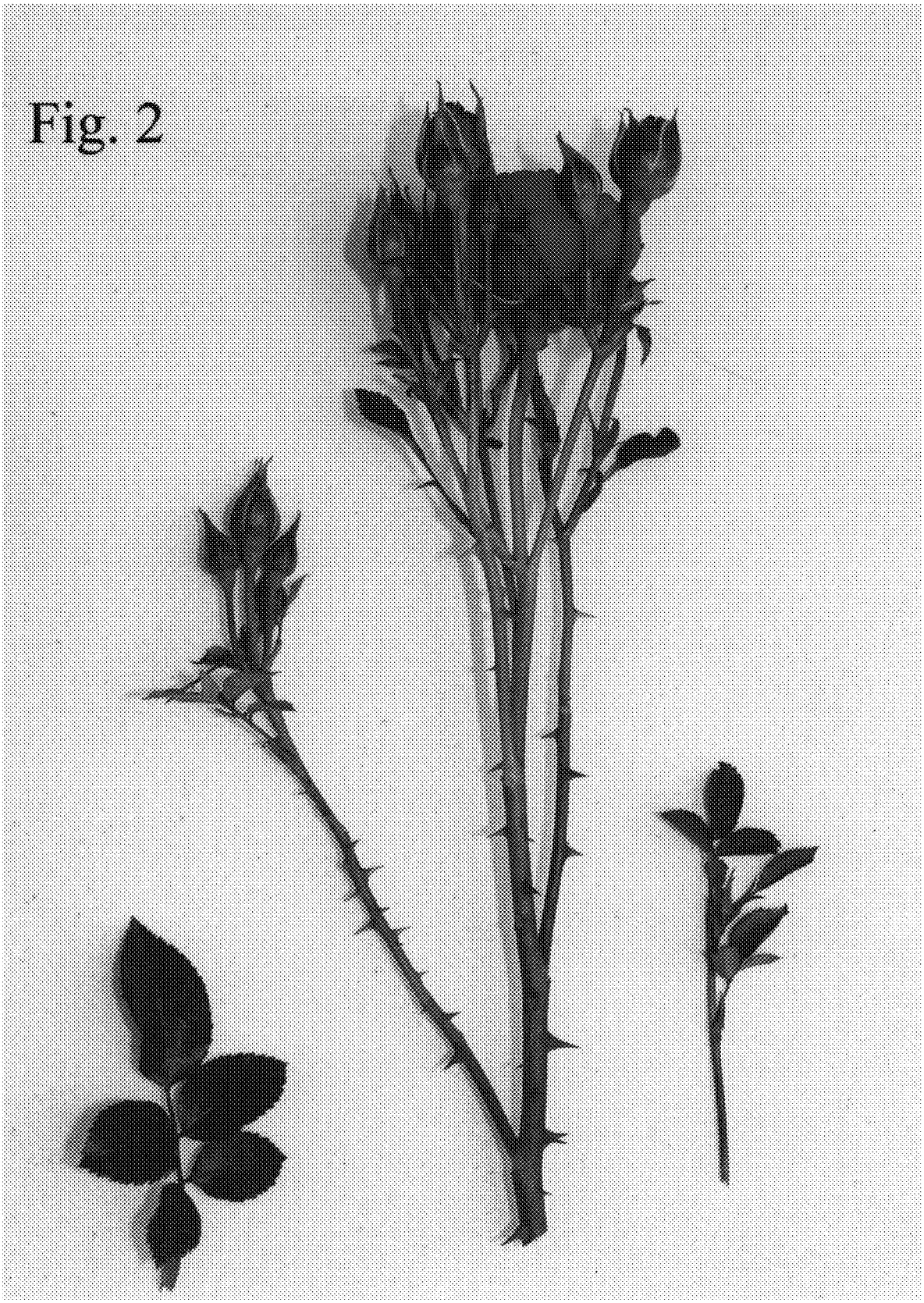

Specifically illustrated in FIG. 2 of the drawings are a cluster of open flowers and un-opened flower buds on the branch, juvenile growth exhibiting anthocyanin, and mature leaves. Plants shown are 2 years of age.

DETAILED DESCRIPTION OF THE VARIETY

The following is a description of 'Poulpar126', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar029', U.S. Plant Pat. No. 16,148 are compared to 'Poulpar126' in Chart 1.

CHART 1

| | 'Poulpar126' | 'Poulpar029' |
|---|---|---|
| Petal Count | 40 | 30 |
| Flower Diameter | 63 mm | 35 mm |
| General Tonality of Flower Color | Red Group 46B | Red Group 53A and Red Group 46A |

FLOWER AND FLOWER BUD

Blooming habit: Continuous.

Flower bud:

*Size.*—Upon opening, 26 mm in length from base of receptacle to end of bud. Bud diameter is 19 mm.

*Bud form.*—Ovoid.

*Bud color.*—As sepals divide petals are Red Group 46A.

*Sepal inner surface.*—Color: Yellow-Green Group 144B. Surface: Lightly pubescent.

*Sepal outer surface.*—Color: Yellow-Green Group 144A with intonations of Greyed-Orange Group 175A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—21 mm long, 9 mm wide.

*Receptacle.*—Texture: Smooth. Size: 10 mm in height, 6 mm wide. Color: Yellow-Green Group 144A with intonations of Greyed-Purple Group 183A. Shape: Campanulate.

*Pedicel.*—Surface: Smooth. Length: 31 mm. Diameter: 3 mm on average. Color: Yellow-Green Group 144A with intonations of Greyed-Orange Group 175A. Strength: Strong.

*Peduncle.*—Length: 3 to 8 cm. Diameter: About mm. Color: Yellow-Green Group 14A with intonations of Greyed-Purple Group 183C. Texture: Smooth.

Flower bud development: Flower buds are borne in clusters of 3 to 9 flower buds per stem.

Flower bloom:

*Fragrance.*—Moderate rose scent.

*Duration.*—The blooms have a duration on the plant of approximately 21 days. Petals fall cleanly away from plant after flowers have fully matured.

*Size.*—Flower diameter is 63 mm when open. Flower depth is 30 mm.

*Flower shape.*—Rosette, very double flower with many slightly overlapping petals of different sizes.

*Shape of flower, side view.*—The upper portion is flat. The lower portion is concave.

Petalage: Under normal conditions, flowers have about 40 petals.

General tonality of flower: Open flowers are Red Group 46B.

Petal color:

*Upon opening, outer petals.*—Upper surface: Red Group 46B. Lower surface: Red-Purple Group N57B.

*Upon opening, inner petals.*—Upper surface: Red Group 46B. Lower surface: Red-Purple Group N57B.

*Basal petal spots, upon opening.*—Upper surface: Yellow Group 4A. Lower surface: Yellow Group 4B.

*After opening, outer petals.*—Upper surface: Red Group 46B. Lower surface: Red-Purple Group N57B.

*After opening, inner petals.*—Upper surface: Red Group 46B. Lower surface: Red-Purple Group N57B.

*Basal petal spots, after opening.*—Upper surface: Yellow Group 4A. Lower surface: Yellow Group 4B.

Petals:

*Petal reflex.*—None.

*Margin.*—Entire and uniform. No undulations.

*Shape.*—Broad and elliptic. Apex shape: Rounded. Base shape: Obtuse.

*Size.*—31 mm (l)×35 mm (w).

*Texture.*—Smooth.

*Thickness.*—Average.

Petaloids: Size: 12 mm (l) by 10 mm (w). Quantity: About 12. Shape: Elliptical with an acute base and rounded apices. Color: The upper surface is Red Group 46B. The lower surface is Red-Purple Group N57B. At the base of the petaloid Yellow Group 4A.

Reproductive flower parts:

*Pollen.*—None observed.

*Anthers.*—Size: 2 mm in length. Color: Yellow Group 4B. Quantity: 44 on average.

*Filaments.*—Color: Yellow Group 8A with intonations of Red Group 38A. Length: 3 mm.

*Pistils.*—Length: 10 mm. Quantity: 22 on average.

*Stigmas.*—Color: Green-White Group 157A.

*Styles.*—Color: Green-White Group 157A.

*Location of stigmas.*—Level in location relative to the length of the filaments and the height of the anthers.

*Hips.*—None Observed.

PLANT

Plant growth: Upright, bushy. Plants are 37 cm in height, and 30 cm wide.

Stems:

*Color of juvenile growth.*—Yellow-Green Group 144A A with intonations of Greyed-Red Group 181A.

*Color of mature growth.*—Yellow-Green Group 144A.

*Length.*—Canes are about 15 cm from the base of the plant to the flowering portion.

*Diameter.*—About 4 mm.

*Internodes.*—On mature canes about 45 mm between nodes.

*Surface texture.*—Young wood: Smooth. Older wood: Smooth.

Long prickles:

*Incidence.*—About 10 prickles per 10 cm of stem.

*Size.*—Average length of prickles on mature stems is 9 mm.

*Shape.*—Upper portion is linear. Lower portion is concave.

*Color.*—Juvenile prickles: Greyed-Red Group 182A. Mature prickles: Greyed-Red Group 182A.

Plant foliage:

*Compound leaf.*—115 mm (l)×67 (w).

*Quantity.*—3 leaves per 10 cm of stem on average.

*Leaf bearing angle to the stem.*—45 degrees.

*Color of juvenile foliage.*—Upper side: Yellow-Green Group 146B with strong intonations of Greyed-Purple Group 183A. Lower side: Yellow-Green Group 146B with strong intonations of Greyed-Purple Group 183A.

*Color of mature foliage.*—Upper side: Yellow-Green Group 146A. Lower side: Yellow-Green Group 146C.

Plant leaves and leaflets:

*Stipules.*—Size: 15 mm long, mm wide. Quantity: 2 per compound leaf. Shape: Linear, slightly broad based with outward extending apices. Margins: Finely serrated. Color:

*Petiole.*—Length: 25 mm. Diameter: About 2 mm. Upper surface color: Yellow-Green Group 144A. Lower surface color: Yellow-Green Group 144A.

*Rachis.*—Length: 25 mm. Upper surface color: Greyed-Purple Group 183B. Lower surface color: Yellow-Green Group 144A.

*Leaflet.*—Quantity: Normally 5 leaflets. Margins: Serrated. Size: Terminal leaflets are about 42 mm long, 25 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar126', substantially as illustrated and described herein, due to its abundant red flowers, disease resistance, and extended period of bloom.

* * * * *